United States Patent [19]

Mizumoto

[11] 4,278,077
[45] Jul. 14, 1981

[54] MEDICAL CAMERA SYSTEM

[75] Inventor: Morihide Mizumoto, Hachioji, Japan

[73] Assignee: Olympus Optical Co., Ltd., Tokyo, Japan

[21] Appl. No.: 60,008

[22] Filed: Jul. 24, 1979

[30] Foreign Application Priority Data

Jul. 27, 1978 [JP] Japan .................. 53/91768

[51] Int. Cl.³ .............................................. A61B 1/00
[52] U.S. Cl. .......................................... 128/4; 128/6; 354/62
[58] Field of Search ...................... 128/3–8, 128/631, 769, 260; 354/62, 63, 131, 135, 126, 234, 235

[56] References Cited

U.S. PATENT DOCUMENTS

| 2,788,390 | 4/1957 | Sheldon | 128/8 |
| 3,329,074 | 7/1967 | Gosselin | 128/4 |
| 3,599,630 | 8/1971 | Sato et al. | 354/62 X |
| 4,085,742 | 4/1978 | Okada | 128/6 X |
| 4,171,897 | 10/1979 | Fujita et al. | 354/234 |

FOREIGN PATENT DOCUMENTS 1482481  4/1967  France ..................... 128/8

Primary Examiner—John D. Yasko

[57] ABSTRACT

A capsule-shaped miniature camera comprising at least one permanent magnet, an induction coil, a lamp serially connected to the induction coil and a shutter device. The induction coil induces an electromotive force when an magnetic field generated by electromagnets outside the camera acts on it. The electromotive force turns on the lamp and drives the shutter device.

8 Claims, 7 Drawing Figures

MEDICAL CAMERA SYSTEM

BACKGROUND OF THE INVENTION

This invention relates to a medical camera system for, for example, an endoscope.

A known camera system of this type comprises a camera attached to the proximal end of an endoscope and an optical system and an illumination device both attached to the distal end of the endoscope. The distal end portion of the endoscope is inserted into a body cavity, and pictures of the interior of the body cavity are taken. According to the medical camera system using the endoscope, every time the optical system and illumination device are put into the body cavity, the patient feels sick with an impulse to vomit.

SUMMARY OF THE INVENTION

It is an object of this invention to provide a medical camera system which can reduce such a feeling of sickness the patient has.

According to this invention there is provided a medical camera system which has a capsule-shaped miniature camera including a coil, an illumination means and a photographying means. The camera is made so small that a patient can swallow. The coil is energized by a magnetic field outside the patient to generate an electromotive force, which actuates the illumination means and photographing means.

DETAILED DESCRIPTION OF THE PREFERRED EMBODIMENTS

Figure 1:
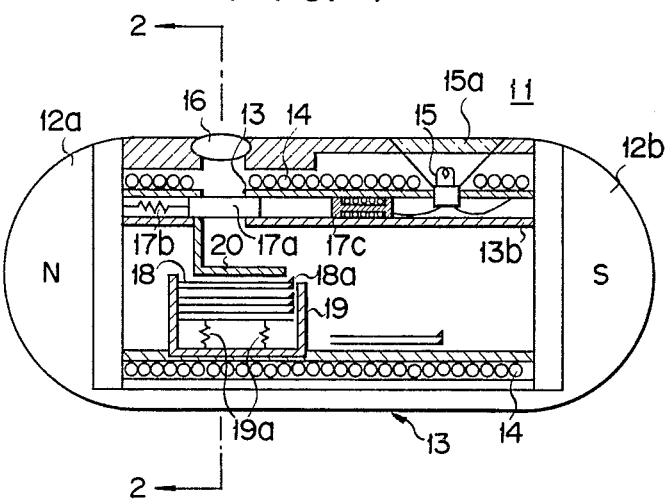
FIG. 1 is a cross sectional view of a capsule-shaped miniature camera used in a medical camera system according to this invention.
Figure 2:
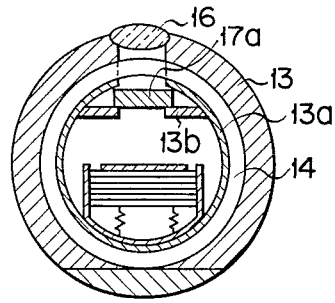
FIG. 2 is a cross sectional view of the camera shown in FIG. 1, taken along line 2—2 in FIG. 1.

A medical camera system according to this invention comprises a capsule-shaped miniature camera. As shown in FIGS. 1 and 2, the capsule-shaped miniature camera 11 comprises a permanent magnet 12, an outer envelope 13 and an inner envelope 13a. The permanent magnet 12 is so disposed that its N pole 12a and its S pole 12b are put on the ends of the outer envelope 13, respectively. The inner envelope 13a is arranged in the outer envelope 13 coaxially therewith. Around the inner envelope 13a a coil 14 is wound.

The outer envelope 13 has an opening or window with a transparent pane 15a. On the inner envelope 13a an illumination means such as a lamp 15 is provided to face the transparent pane 15a. The outer envelope 13 has another opening in which a lens 16 is fitted in a liquid-tight fashion. Disposed right below the lens 16 and within the inner envelope 13a is a shutter plate 17a. The shutter plate 17a is slidably inserted in a space between the inner envelope 13a and a support plate 13b extending within the inner envelope 13a in the lengthwise direction of the inner envelope 13a. It is biased by a spring 17b to close two openings which are concentrically made in the inner envelope 13a and the support plate 13b, respectively. When attracted to an electromagnet 17c, the shutter plate 17a opens the openings. The shutter plate 17a, spring 17b and electromagnet 17c constitute a shutter device 17.

Below the shutter plate 17a there is disposed a film box 19 in which unexposed films 18 are piled one upon another. Coil springs 19a are provided on the bottom of the film box 19 to push up the films 18. Each film 18 has a projection 18a on one of its four edges. A film feeding member 20 is secured to the shutter plate 17a in such a manner as to come into contact with the projection 18a of the uppermost film 18 and feed the film 18 outside the film box 19 every time the shutter plate 17a is attracted to the electromagnet 17c and thus expose the next film 18 to light.

Figure 3:
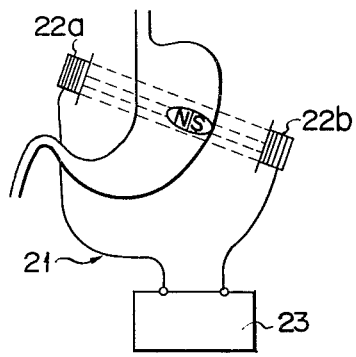
FIG. 3 illustrates how the medical camera system of this invention is used.

The capsule-shaped miniature camera 11 is actuated by such a magnetic field generating apparatus 21 as illustrated in FIG. 3. The apparatus 21 comprises a pair of electromagnets 22a and 22b and a current source 23 for supplying current to the magnets 22a and 22b. The current source 23 generates a gradually increasing current and is constituted by, for example, a power source and a current control circuit. The current control circuit is constituted by, for example, a resistor or a semiconductor circuit.

Now it will be described how the medical camera system comprising the capsule-shaped miniature camera 11 and the magnetic field generating apparatus 21 is operated to take pictures of, for instance, the interior of a stomach.

First, the camera 11 is swallowed down to the patient's stomach. Then, the electromagnets 22a and 22b on the patient's sides so as to sandwich his or her stomach as shown in FIG. 3. The current source 23 supplies current to both electromagnets 22a and 22b, thereby generating a magnetic field between the magnets 22a and 22b. The magnetic field acts on the permanent magnets 12 of the miniature camera 11 and thus moves the camera 11 in the stomach toward the electromagnet 22a or 22b of the apparatus 21. Thus, the miniature camera 11 can be moved to a desired position in the stomach by changing the positions of the electromagnets 22a and 22b.

When the camera 11 is brought to a desired position in the stomach, it is ready to take pictures. To take pictures, the current supplied to the electromagnets 22a and 22b is gradually increased by the current control circuit of the current source 23. As the magnetic flux is intensified, the coil 14 of the camera 11 generates a voltage which is proportional to $\Delta\phi/\Delta t$, where $\Delta\phi$ denotes a change of magnetic flux intensity and $\Delta t$ a period of time during which such a change takes place. Connected in series to the coil 14, the lamp 15 is turned on. The electromagnet 17c, which is connected also in series to the coil 14, is excited to attract the shutter plate 17a against the spring 17b.

Figure 4:
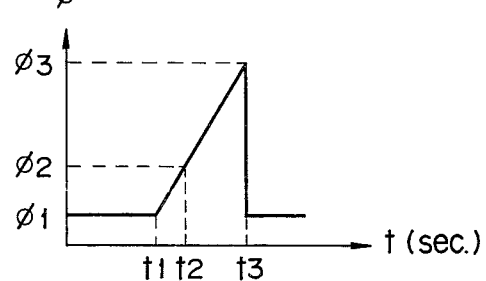
FIG. 4 is a graph showing how the intensity of magnetic flux applied on the camera is varied while the medical camera system is operated.

The shutter plate 17a slides toward the electromagnet 17c and opens the openings of the inner envelope 13a and the support plate 13b. An image of the interior of the stomach, which is illuminated by the lamp 15, is therefore focused on the uppermost film 18. The time during which the film 18 is exposed is determined by, as illustrated in FIG. 4, the period from time $t_2$ to time $t_3$ during which the magnetic flux intensity changes from $\phi_2$ to $\phi_3$. As soon as such exposure period elapses, the current control circuit of the current source 23 stops increasing the current supplied to the electromagnets 22a and 22b. As a result, the intensity of the magnetic flux stops changing, and the coil induces no voltage. Consequently, the lamp 15 is turned off, and the electromagnet 17c is no longer excited. The shutter plate 17a is pulled by the spring 17b to close the openings made in the inner envelope 13a and the support plate 13b. Thus ends the exposure of the film 18.

When the current supplied to the electromagnets 22a and 22b is gradually increased again, the lamp 15 is turned on, and the shutter plate 17a is moved toward the electromagnet 17c. The film feeding member 20, which is secured to the shutter plate 17a, is therefore moved to feed the exposed film 18 outside the film box 19 and, at the same time, to expose the next film 18 to the light coming through the lens 16 and the openings made in the inner envelope 13a and the support plate 13b.

The camera 11 is so small that the patient has almost no pain when he swallows it. Once in a body cavity such as stomach, the camera 11 is moved, magnetically between the electromagnets 22a and 22b set outside the patient, and does not cause him or her pain when it is operated.

Figure 5:
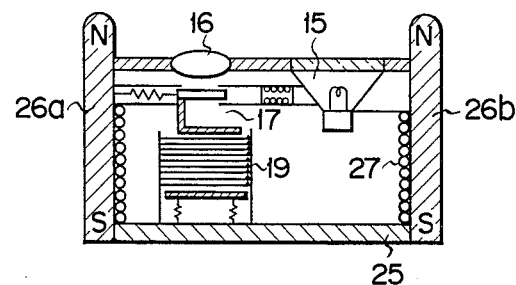
FIG. 5 is a cross sectional view of another capsule-shaped miniature camera according to this invention, in which a pair of permanent magnets are disposed on the sides of a camera envelope.
Figure 6:
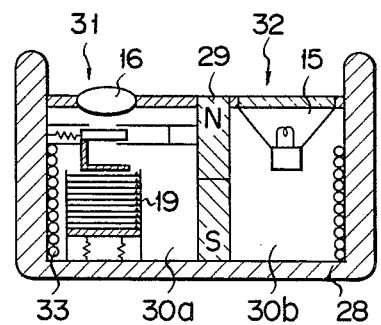
FIG. 6 is a cross sectional view of still another capsule-shaped miniature camera according to this invention, in which a permanent magnet is disposed in the middle of a camera envelope.
Figure 7:
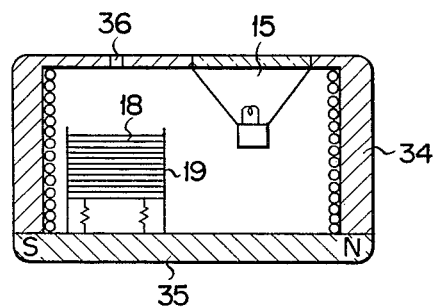
FIG. 7 is a cross sectional view of a further capsule-shaped miniature camera according to this invention, whose opticaly photographying means is a pinhole made in a camera envelope.

The capsule-shaped miniature camera 11 may have such various structures as illustrated in FIGS. 5 to 7.

The camera shown in FIG. 5 comprises an envelope 25, a pair of permanent magnets 26a and 26b provided on the ends of the envelope 25, a lamp 15 disposed within the envelope 25 and a lens 16 fitted in an opening made in the envelope 25. The permanent magnets 26a and 26b are so arranged to have their ends of the same polarity projecting a little from the envelope 25. The camera further has an induction coil 27 which is provided between the permanent magnets 26a and 26b. The camera further comprises a shutter device 17, a film box 19 and a film feeding member 20 which are disposed within the envelope 25 and which are of the same structure as those of the camera shown in FIGS. 1 and 2. The camera is swallowed into a body cavity, the N poles of its permanent magnets 26a and 26b come into touch with the wall of the body cavity when a magnetic field is generated by a pair of electromagnets outside the patient. While the N poles of the magnets 26a and 26b are in contact, neither the lamp 15 nor the lens 16 touches the wall of the body cavity, the interior of the body cavity can be photographed at a close distance.

The camera shown in FIG. 6 comprises an envelope 28 which is partitioned by a permanent magnet 29 into two chambers 30a and 30b. Provided in the chamber 30a is a photographing mechanism 31 comprising a lens 16, a shutter device 17, a film box 19 and a film feeding member 20. The shutter device 17, film box 19 and film feeding member 20 are of the same structure as those of the camera shown in FIGS. 1 and 2. Disposed in the chamber 30a is an illumination device 32 comprising a lamp 15. An induction coil 33 is placed in the envelope 28 so that its outer periphery is in total contact with the four sides of the envelope 28. The end walls project a little from the envelope 28, so that neither the lens 16 nor the illumination device 32 touches the wall of a body cavity.

The cameras of FIGS. 5 and 6 are operated in the same manner as is the camera illustrated in FIGS. 1 and 2.

The camera shown in FIG. 7 comprises an envelope 34 and a permanent magnet 35. The permanent magnet 35 extends in the lengthwise direction of the envelope 34 and is secured to the envelope 34. That portion of the envelope 34 which is diametrically opposite to the magnet 35 has a pinhole 36 and a window both covered with transparent panes. Within the envelope 34, a film box 19 is disposed to face the pinhole 36, and a lamp 15 to face the window. Every time the lamp 15 is turned on, an image of the interior of the body cavity is focused on a film 18 in the film box 19. The amount of light emitted by the lamp 15 can be controlled.

As mentioned above, according to this invention, an induction coil provided in a capsule-shaped miniature camera which has been swallowed into a body cavity induces a voltage when a magnetic field generated by electromagnets outside the patient acts on the induction coil. The voltage thus induced turns on a lamp disposed within the camera and operates a shutter disposed within the camera, whereby the interior of the body cavity is photographed. Such a medical camera system rarely makes the patient feel sick with an impulse to vomit and thus facilitates an easy photographing of a body cavity interior.

What is claimed is:

1. A medical camera system comprising a capsule-shaped miniature camera being received in a body cavity and a magnetic field generating device including electromagnet means disposed outside a body and a power supply unit for supplying an energizing current to the electromagnet means to permit the electromagnet means to generate a magnetic field, said miniature camera comprising an envelope provided with at least one permanent magnet, a coil disposed in the envelope for inducing an electromotive force from the magnetic field generated by the magnetic field generating device, illumination means provided in the envelope and excited by the electromotive force of the coil for illuminating an object, a shutter device operated by the electromotive force of said coil, a film box disposed in the envelope for containing films, and an optical system for focusing an image of the illuminated object on one of the films contained in the film box.

2. A medical camera system according to claim 1, wherein said miniature camera includes a permanent magnet whose north and south poles are disposed on both ends of said envelope, respectively.

3. A medical camera system according to claim 1, wherein said miniature camera includes a pair of permanent magnets, north and south poles of one of which face the north and south poles of the other respectively.

4. A medical camera system according to claim 1, wherein said permanent magnet is disposed on a central portion of the envelope to partition the envelope into two chambers one of which houses said illumination means and the other of which houses said optical system and said film box.

5. The medical camera system according to claim 1, wherein said envelope comprises by an outer envelope and an inner envelope, and said coil is wound about the inner envelope.

6. The medical camera system according to claim 1, wherein said shutter device comprises a shutter plate which is slidably disposed between said optical system and said film box and an electromagnet which is connected to said coil and excited by the electromotive force of said coil to attract the shutter plate.

7. The medical camera system according to claim 6, wherein said shutter device includes a film feeding member which operates together with said shutter plate to feed a film outside said film box.

8. The medical camera system according to claim 1, wherein said illumination means and optical system are recessed from the outer periphery of said envelope.

* * * * *